US00PP14085P29

(12) United States Plant Patent
Lemon

(10) Patent No.: US PP14,085 P2
(45) Date of Patent: Aug. 19, 2003

(54) GERANIUM PLANT NAMED 'GLOBAL SOFT PINK'

(75) Inventor: David Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,015

(22) Filed: Sep. 17, 2002

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Webb Ziesenhiem Logsdon Orkin & Hanson, P.C.

(57) ABSTRACT

A new and distinct very free flowering ivy geranium plant with distinctive soft pink colored flowers above medium green foliage and having very good heat tolerance.

1 Drawing Sheet

Botanical classification: *Pelargonium×peltatum* (ivy geranium).

Varietal denomination: 'Global Soft Pink'.

BACKGROUND OF THE INVENTION

The present invention comprises a new and distinct cultivar of *Pelargonium×peltatum* known by the varietal name 'Global Soft Pink'. The new variety was discovered in a selected breeding program in Lompoc, Calif. as Breeder No. 4DG955. The new variety is a result of cross breeding of 'Guimongol' (female) (U.S. Plant Pat. No. 9,352) and 'Belladona' (male) (unpatented). The new variety exhibits similar plant type to both parents and a flower color intermediate the parents' flower colors. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 12 weeks from a rooted cutting to flowering in a 10 inch pot. The response time was determined on plants grown in soilless media employing constant fertilizer 200–250 parts per million of nitrogen and potassium in full light. Three cuttings planted in a pot and pinched at four weeks produces a finished hanging basket.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants were about 12 weeks old when described. The color readings were taken on a plant under 65–85 foot candles of fluorescent cool white light. Color references are primarily to The R.H.S. Colour Chart of The Royal Horticultural Society of London.

PLANT

Form: Compact, cascading mound.
Height: 15 cm from media surface to top of foliage in a 17 cm pot.
Diameter: 40 cm.
Strength: Does not require artificial support.
Rooting time: Roots visible to outside of a dirt plug in 10–14 days.
Leaves:
- *Arrangement.*—Alternate.
- *Stipules.*—Two per node.
- *Size.*—Length: 4.0–5.0 cm. Width: 5.0–6.0 cm. Zone: 7 mm from petiole attachment; zone is 5 mm wide.
- *Shape.*—Reniform; cordate base, pointed apex.
- *Margin.*—Entire with lobes.
- *Texture.*—Leathery; slightly pubescent.
- *Color.*—Upper surface: 137B. Lower surface: 137C. Zone: Faint, noticeable on some leaves; ranges from 187A to 147A.
- *Ribes and veins.*—Venation: Palmate. Color: 146C.

Petioles:
- *Color.*—146B.
- *Length.*—2.3–3.6 cm.

Stem:
- *Color.*—146B.
- *Length.*—20 cm.
- *Internode length.*—2.5–5.5 cm.

THE BUD

Shape when no color showing:
- *Overall.*—Elongated, elliptical cluster.
- *Individual bud.*—Elliptical.

Size when no color showing:
- *Overall.*—3.5–4.25 cm across cluster.
- *Individual bud.*—1.0–1.5 cm long, 0.7 cm wide.

Number of buds per cluster: 8–10.
Color (Just prior to sepals parting at tips): 65D.

INFLORESCENCE

Blooming habit: Continuous flowering throughout growing season; semi-double flowers.
Size of umbel: 8–10 cm in diameter, 5 cm in depth.
Borne: Umbel, flowers on pedicel, pedicel on peduncle, 5.5–8.5 cm above foliage.

Flowers:

*Form.*—Flat to slightly cupped; petals overlap to give a ruffled appearance.

*Number of flowers per umbel.*—7–12.

*Size.*—Diameter: 5.0–5.5 cm. Depth: 1.0–2.0 cm.

Petals:

*Color.*—Upper surface: Starting at outer edge, the color progresses from 65A to 49B and 50D at base of petal. Some petals have highlights of 73B and 73C at the center of the petal. All petals have an eye, but it is more pronounced on some upper petals and ranges in intensity from 61B to 61C with areas of 61D and 49A at outer edges of the petal at the base. Darker veining of 61A and 59A is present. The eye of the petals that are less prominent ranges in color from 63B to 50B to 61D. Lower surface: 65D shading to 49C at base of petal. Dark veining shows through from top. Shape: Teardrop; pointed base, rounded apex. Size: 2.3–3.5 cm Long; 1.4–2.2 cm wide. Margin: Entire. Number per flower: 18–22. Texture and appearance: Highly reflective, smooth, velvety.

Tonality from a distance: Flowers are a soft blue-pink with a bright glowing salmon center highlighted by dark burgundy veining atop a mound of medium green foliage.

Petaloids:

*Quantity.*—0–5.

*Shape.*—Irregular; some twisted; tubular.

*Color.*—Same as petals.

Sepals:

*Quantity.*—5.

*Shape.*—Narrow; nearly parallel at base, narrows to point pointed; apex, entire margin.

*Size.*—1.4–1.5 cm long; 0.3–0.6 cm wide.

*Color.*—Upper and Lower Surface: 144B.

Pedicel:

*Length.*—2.0–2.75 cm.

*Color.*—146B with blush of 61B.

Peduncle:

*Length.*—9–17 cm.

*Color.*—146B with older peduncles having blush of 61B.

Lasting quality: Umbels last 7–14 days, individual flowers last 7 days.

Disease/pest resistance: No susceptibility to diseases or pests has been noted to date.

REPRODUCTIVE ORGANS

Stamens:

*Anthers.*—2.0–3.0 mm in length.

*Filaments.*—Length: 1.0–1.4 cm. Color: Predominantly white; some with pink blush. Pollen: Rusty orange.

Pistils:

*Number.*—One.

*Length.*—0.7–1.2 cm.

*Stigma.*—Number: One. Color: Red purple.

*Style.*—Length: 0.3–0.5 cm. Color: Pale pink or white.

*Ovaries.*—Superior; heavy pubescence; 0.4–0.6 cm long; 0.15–0.20 cm wide; pale green.

Fruit: None observed.

I claim:

1. A new and distinct variety of geranium plant substantially as shown and described.

* * * * *

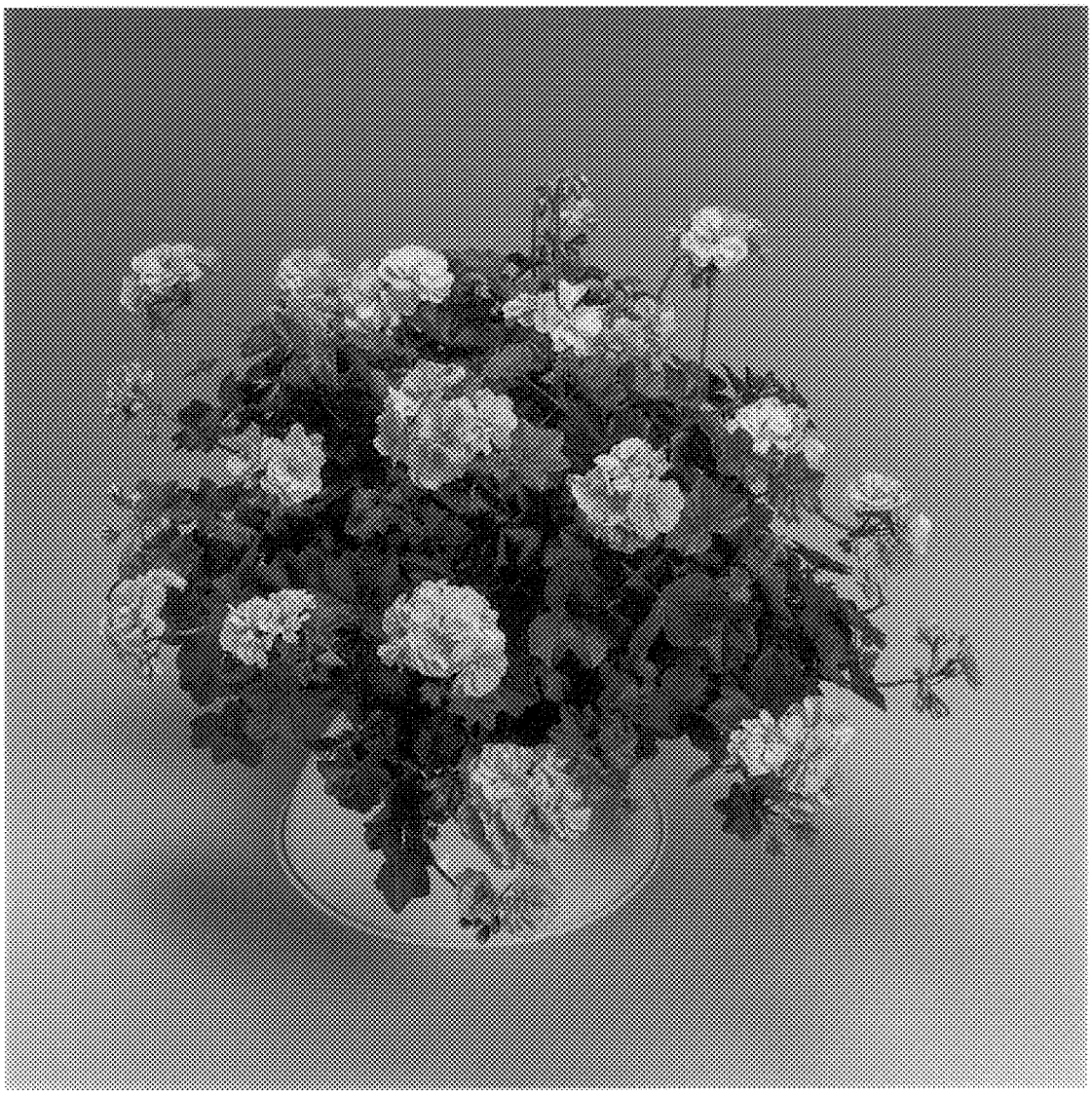

UNITED STATES PATENT AND TRADEMARK OFFICE

CERTIFICATE OF CORRECTION

PATENT NO. : PP 14,085 P2
DATED : August 19, 2003
INVENTOR(S) : David Lemon

It is certified that error appears in the above-identified patent and that said Letters Patent is hereby corrected as shown below:

Column 3,
Line 32, “point pointed; apex” should read -- point; pointed apex --.

Signed and Sealed this

Twenty-third Day of March, 2004

JON W. DUDAS
*Acting Director of the United States Patent and Trademark Office*